(12) United States Patent
Hashizume et al.

(10) Patent No.: US 10,082,456 B2
(45) Date of Patent: Sep. 25, 2018

(54) PHOTOTHERMAL CONVERSION SPECTROSCOPIC ANALYZER

(71) Applicant: Hitachi, Ltd., Chiyoda-ku, Tokyo (JP)

(72) Inventors: Jiro Hashizume, Tokyo (JP); Kei Takenaka, Tokyo (JP); Takanori Aono, Tokyo (JP)

(73) Assignee: Hitachi, Ltd., Tokyo (JP)

(*) Notice: Subject to any disclaimer, the term of this patent is extended or adjusted under 35 U.S.C. 154(b) by 73 days.

(21) Appl. No.: 14/962,334

(22) Filed: Dec. 8, 2015

(65) Prior Publication Data

US 2016/0178506 A1 Jun. 23, 2016

(30) Foreign Application Priority Data

Dec. 17, 2014 (JP) ................................. 2014-254662

(51) Int. Cl.
*G01N 21/17* (2006.01)
(52) U.S. Cl.
CPC ... *G01N 21/171* (2013.01); *G01N 2021/1712* (2013.01)
(58) Field of Classification Search
CPC ....................... G01N 21/171; G01N 2021/1712
See application file for complete search history.

(56) References Cited

U.S. PATENT DOCUMENTS

| | | | | |
|---|---|---|---|---|
| 4,938,593 A | * | 7/1990 | Morris | G01N 21/171 356/344 |
| 2006/0109465 A1 | * | 5/2006 | Fukuzawa | G01N 21/645 356/417 |
| 2006/0181708 A1 | * | 8/2006 | Takahashi | G01N 21/171 356/432 |
| 2008/0030735 A1 | * | 2/2008 | Kitamori | G02B 21/0004 356/432 |
| 2008/0123099 A1 | * | 5/2008 | Takahashi | G01N 21/171 356/450 |
| 2009/0027654 A1 | * | 1/2009 | Takahashi | G01N 21/00 356/36 |
| 2010/0060981 A1 | * | 3/2010 | Yamauchi | G01N 21/171 359/386 |
| 2010/0159451 A1 | * | 6/2010 | Ikebukuro | C12Q 1/6804 435/6.13 |
| 2011/0007317 A1 | * | 1/2011 | Ikebukuro | B01L 3/5027 356/432 |
| 2012/0212599 A1 | * | 8/2012 | Murakami | G02B 21/0036 348/79 |

(Continued)

FOREIGN PATENT DOCUMENTS

| | | |
|---|---|---|
| JP | 4-369467 A | 12/1992 |
| JP | 2004-301520 A | 10/2004 |
| JP | 2005-164614 A | 6/2005 |

*Primary Examiner* — Dominic J Bologna
(74) *Attorney, Agent, or Firm* — Crowell & Moring LLP

(57) ABSTRACT

The present invention includes: an excitation light source; a probe light source; a filter that mutually multiplexes a probe light emitted from the probe light source and an excitation light emitted from the excitation light source to a same optical axis; a condenser lens that focuses the excitation light and the probe light; a sample cell that stores a sample; a reflection member that is disposed on an inner wall of the sample cell and reflects the probe light; and a detector that detects the probe light reflected at the reflection member.

1 Claim, 5 Drawing Sheets

(56) References Cited

U.S. PATENT DOCUMENTS

2014/0118731 A1\* 5/2014 Ayers .................... G01J 3/0237
356/301
2015/0036145 A1\* 2/2015 Cichos ................. G01N 21/171
356/451

\* cited by examiner

PHOTOTHERMAL CONVERSION SPECTROSCOPIC ANALYZER

CLAIM OF PRIORITY

The present application claims priority from Japanese Patent application serial No. 2014-254662, filed on Dec. 17, 2014, the content of which is hereby incorporated by reference into this application.

BACKGROUND OF THE INVENTION

Field of the Invention

The present invention relates to a photothermal conversion spectroscopic analyzer, and particularly relates to the photothermal conversion spectroscopic analyzer using a thermal lens effect.

Description of the Related Art

When a sample is irradiated with a focused light, the sample absorbs the light and temperature rises locally. With this temperature rise, a refraction index of the sample is changed. In many substances, there is an optical effect such as a concave lens generated near a light focusing portion of the sample because the refraction index is decreased due to temperature rise. This effect is generally called a thermal lens effect, and sample measurement utilizing this effect is used as a high-sensitivity measuring method for a non-fluorescent substance.

FIG. 6A is a schematic configuration diagram illustrating an exemplary related art in which a photothermal conversion spectroscopic analyzer 302 uses a transmission optical system using the above-described thermal lens effect (JP-2005-164614-A). In FIG. 6A, an excitation light L1 emitted from an excitation light source 101 and a probe light L2 emitted from a probe light source 102 are multiplexed on a same optical axis at a first filter 103, and the multiplexed light enters a sample 109 contained in a sample cell 107 after having passed through a first condenser lens 106, such as an objective lens. The excitation light L1 has a characteristic to be partly absorbed in the sample 109. Therefore, the excitation light L1 focused in the sample 109 by the first condenser lens 106 locally heats the sample 109 in a light focusing area. Then, the excitation light L1 is absorbed at a third filter 110. On the other hand, a probe light L2 passing through the optical axis same as the excitation light L1 has a spreading angle of a light beam irradiated to a detector 111 expanded by a thermal lens generated at the light focusing portion of the excitation light L1 in the sample 109. A change amount of the spreading angle of the probe light L2 is proportional to concentration of the sample 109, and an incident light amount with respect to the detector 111 is changed. Therefore, the sample concentration can be measured from a detection signal of the detector 111.

FIG. 6B is a schematic configuration diagram illustrating an exemplary related art in which a photothermal conversion spectroscopic analyzer 303 uses a reflection optical system (JP-04-369467-A).

Proposed is the photothermal conversion spectroscopic analyzer 303 using the reflection optical system in which a laser beam having passed through a sample is reflected at a reflector and made to enter a light focusing optical system, and then analysis is performed by utilizing the reflected light. According to JP-04-369467-A, a single beam method in which a probe light L2 is also used as an excitation light is adopted, and the probe light L2 is focused by a first condenser lens 106 to a reflector 113 disposed outside the sample 109 and the sample cell 107. The probe light L2 reflected at the reflector 113 is guided by a filter 121 toward a detector 124 formed of a second condenser lens 118, a cylindrical lens 122, and a light receiving element 123, and then a thermal lens signal is measured.

SUMMARY OF THE INVENTION

According to the photothermal conversion spectroscopic analyzing method disclosed in JP-2005-164614-A, there is a problem in which an entire optical system is large-sized.

On the other hand, according to the reflection optical system in JP-04-369467-A, the optical system can be downsized by integrating the optical system on one side of the sample 109. Further, since the probe light L2 reciprocates in the sample 109, higher sensitivity can be achieved compared to the transmission optical system.

Meanwhile, the excitation light L1 and the probe light L2 are slightly absorbed in a component other than the sample 109 where these lights pass through, thereby deteriorating optical properties and causing noise of a signal. Influence therefrom is largely given to the sample cell 107 where the excitation light L1 and the probe light L2 that are focused by the first condenser lens 106 and have high light density pass through. To achieve high-sensitivity analysis for the sample 109, it is important to have a short optical path length that passes through the sample cell 107.

However, the probe light L2 having passed through the sample cell 107 is reflected at the reflector 113 and passes through the sample cell 107 again. Therefore, there may be a problem in which noise of the signal is doubled compared to the invention disclosed in JP-2005-164614-A using the transmission optical system.

The present invention is made in view of the above-described problems in the related arts, and directed to providing a reflection-type photothermal conversion spectroscopic analyzer capable of performing high-sensitivity sample analysis.

To achieve the above object, a photothermal conversion spectroscopic analyzer according to the present invention includes: an excitation light source; a probe light source; a first filter configured to mutually multiplex a probe light emitted from the probe light source and an excitation light emitted from the excitation light source to a same optical axis; a first condenser lens configured to focus the excitation light and the probe light; a sample cell configured to store a sample; a reflection member disposed on an inner wall of the sample cell irradiated with the probe light having passed through the sample, and configured to reflect the probe light; and a detector configured to detect the probe light reflected at the reflection member, wherein the sample contacts the reflection member.

To achieve the above object, a photothermal conversion spectroscopic analyzer according to the present invention includes: an excitation light source; a probe light source; a first filter configured to mutually multiplex a probe light emitted from the probe light source and an excitation light emitted from the excitation light source to a same optical axis; a second filter configured to divide the probe light into a first probe light and a second probe light; a reflector configured to reflect one of the divided probe lights; a first condenser lens configured to focus the other one of the divided probe lights and the excitation light; a sample cell configured to store a sample; a reflection member disposed on an inner wall of the sample cell irradiated with the probe light having passed through the sample, and configured to reflect the probe light; and a detector configured to detect a probe light obtained by multiplexing the first probe light reflected at the reflector and the second probe light reflected at the reflection member, wherein the sample contacts the reflection member.

To achieve the above object, preferably, an excitation light irradiation adjustment unit to adjust both or one of a position and a diameter of the excitation light irradiated to the sample is provided.

To achieve the above object, preferably, a probe light irradiation adjustment unit to adjust both or one of a position and a diameter of the probe light irradiated to the sample is provided.

According to the present invention, size reduction and high sensitivity can be achieved in the photothermal conversion spectroscopic analyzer.

DESCRIPTION OF THE PREFERRED EMBODIMENTS

Embodiments of the present invention will be described below with reference to the accompanying drawings.

First Embodiment

Figure 1:
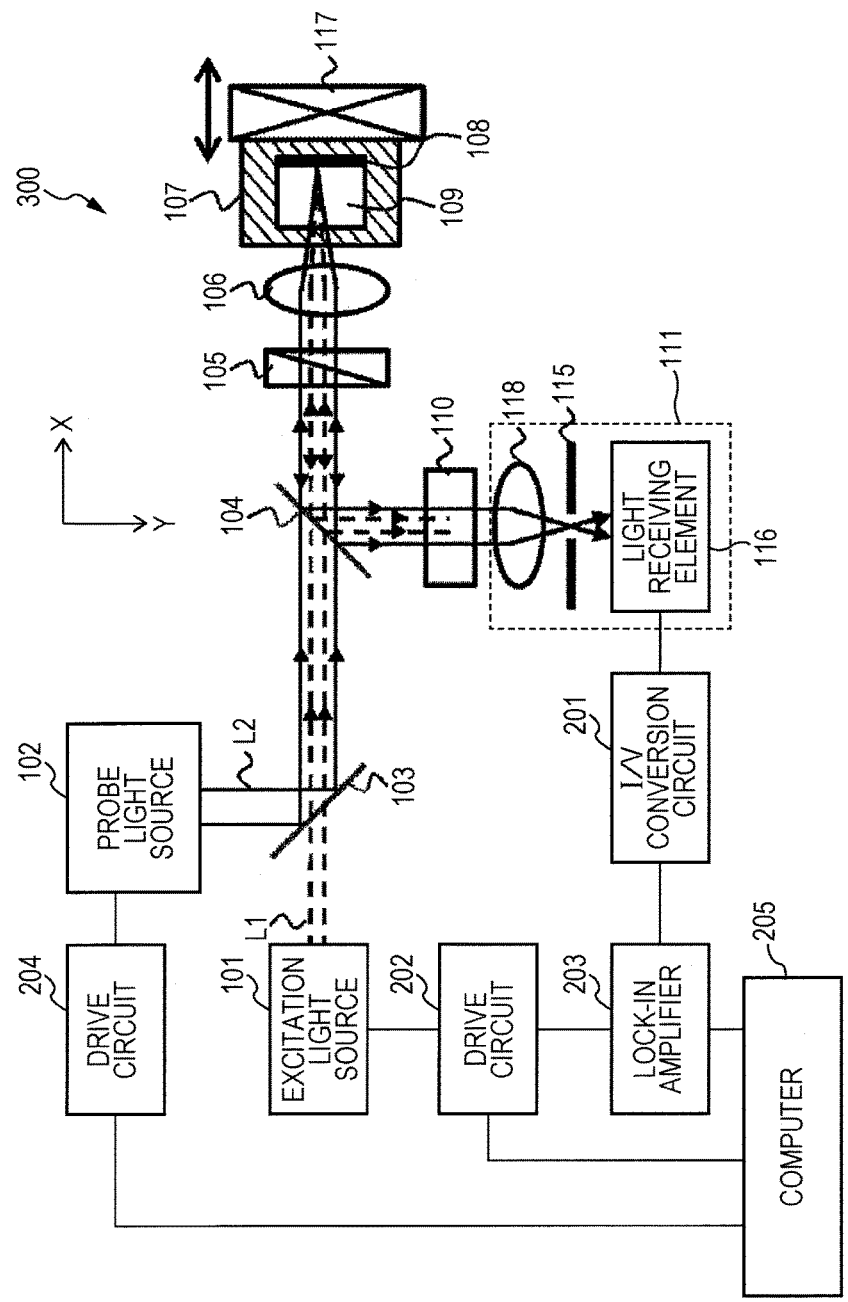
FIG. 1 is a diagram illustrating a photothermal conversion spectroscopic analyzer 300 according to a first embodiment.

FIG. 1 is a diagram illustrating a photothermal conversion spectroscopic analyzer 300 according to a first embodiment of the present invention.

An excitation light L1 emitted from an excitation light source 101 passes through a first filter 103, and a probe light L2 emitted from a probe light source 102 is reflected at the first filter 103. Then, these lights are multiplexed on a same optical axis and the multiplexed light passes through a second filter 104 and a first quarter wavelength plate 105.

The excitation light L1 having passed through the first quarter wavelength plate 105 is focused by a first condenser lens 106 in a sample 109 inside a sample cell 107, and then reflected at a reflection member 108. Inside the sample 109, a so-called thermal lens is formed based on a photothermal conversion phenomenon in which the excitation light L1 is partly absorbed and heat is generated. The excitation light L1 reflected at the reflection member 108 passes through the first condenser lens 106 and the first quarter wavelength plate 105. After that, the excitation light L1 is subsequently reflected at a second filter 104 and absorbed by a third filter 110. In the drawing, a direction corresponding to an optical axis direction of the first condenser lens 106 and also a light traveling direction from the first condenser lens 106 to the sample 109 is set as an X-axis direction. A direction corresponding to a direction vertical to the X-axis and also a traveling direction of the excitation light L1 after being reflected at the second filter 104 is set as a Y-axis direction.

Figure 2:
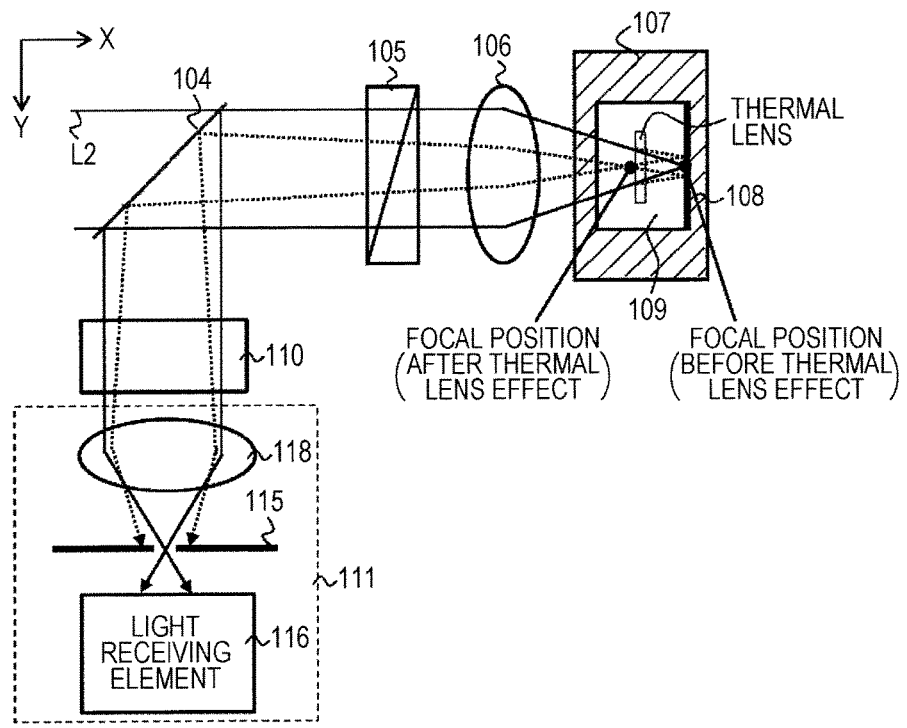
FIG. 2 is an explanatory diagram for a light beam of a probe light when a thermal lens is generated inside a sample.

FIG. 2 is an explanatory diagram for a light beam of the probe light L2 when the thermal lens is generated inside the sample 109.

FIG. 2 illustrates a trajectory of the light beam of the probe light L2 in the case where a light focusing position of the probe light L2 coincides with the reflection member before the thermal lens is generated. Note that the trajectory of the light beam changed by the thermal lens generation is indicated by dotted lines.

As illustrated in FIG. 2, the probe light L2 having passed through the second filter 104 and the first quarter wavelength plate 105 is focused by the first condenser lens 106, and then irradiated to the sample 109.

In the case where the thermal lens is formed by the excitation light L1 inside the sample 109, a light focusing angle of the probe light L2 having passed through the thermal lens becomes large as illustrated by the light beam of the dotted lines in the drawing. In other words, a light flux of the probe light L2 having passed through the thermal lens broadens. The probe light L2 reflected at the reflection member 108 passes through the first condenser lens 106 again, passes through the first quarter wavelength plate 105 as a weak divergent light, and is reflected at the second filter 104. The probe light L2 reflected at the second filter 104 passes through the third filter 110 and is focused by a second condenser lens 118. A pinhole 115 is disposed at a focusing point of the probe light L2 when the thermal lens is not generated. Therefore, a light flux of the probe light L2 having passed through the second condenser lens 118 as the weak divergent light is not sufficiently focused at the pinhole 115 position, and the light flux is partly lost at the pinhole 115 and then irradiated onto a light receiving element 116. In other words, a light amount of the probe light L2 that passes through the pinhole 115 and is detected by the light receiving element 116 is changed proportional to a light amount of the excitation light L1 absorbed in the sample 109.

A current signal of the probe light L2 received by the detector 111 is converted to a voltage signal at a current/voltage conversion circuit 201, and received in a lock-in amplifier 203, and then measured together with a reference signal from a drive circuit 202 that controls a light amount of the excitation light L1 output from the excitation light source 101. A signal indicating a measurement result output from the lock-in amplifier 203 is received in a computer 205, and the sample 109 is analyzed.

Meanwhile, in the case where the excitation light source 101 is a light source that cannot perform modulation at a high speed such as gas laser, a device such as a chopper that can modulate, at a high speed, an optical intensity of the excitation light L1 output from the excitation light source 101 may be disposed between the excitation light source 101 and the first filter 103. At this point, a reference signal from a chopper control device is used in the lock-in amplifier 203 instead of the reference signal from the drive circuit 202.

Meanwhile, the reflection member 108 disposed on an inner wall of the sample cell 107 contacts the sample 109 in the first embodiment. Therefore, the excitation light L1 reciprocates only in a surface of the sample cell 107 close to the first condenser lens 106 in a component where the excitation light L1 focused by the first condenser lens 106 passes through. Therefore, compared to the conventional reflection optical system in which the excitation light L1 passes through two surfaces of the sample cell 107 in a reciprocating manner, deterioration of optical properties caused by absorption of the excitation light L1 by the sample cell 107 can be suppressed while keeping a characteristic of being capable of performing high-sensitivity analysis for the sample 109.

In the photothermal conversion spectroscopic analyzer 300 using the reflection optical system, when the focusing position of the probe light L2 and the position of the reflection member 108 are changed in the optical direction (X-axis), a signal detected by the detector 111 is deteriorated. Therefore, in the case of using a detachable type sample cell 107, for example, readjustment of the sample cell 107 and the focal position of the probe light L2 is needed when the sample cell 107 is replaced.

A method of adjusting the position of the sample cell 107 in the optical axis direction in the photothermal conversion spectroscopic analyzer 300 according to the present embodiment will be described.

Figure 3:
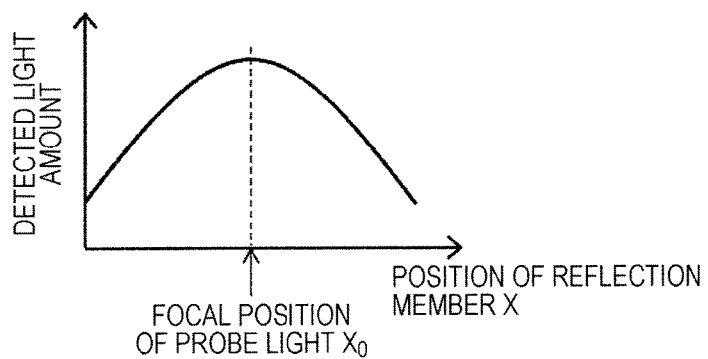
FIG. 3 is a diagram illustrating a relation between a position of a reflection member and a light amount of the probe light detected by a detector.

FIG. 3 is a diagram illustrating a relation between the position of the reflection member 108 and a light amount of the probe light L2 detected by a detector 111.

When there is the pinhole 115 to focus the probe light L2 by the second condenser lens 118, in the case where the position of the reflection member 108 of the sample cell 107 is deviated in either positive or negative optical axis (X-axis) direction from a focusing position X0 of the probe light L2, a focusing angle/divergent angle of the probe light L2 that has been reflected at the reflection member 108 and passed through the first condenser lens 106 again is changed, and a light flux of the probe light L2 irradiated onto the pinhole 115 is broadened. As a result, the light amount of the probe light L2 detected at the light receiving element 116 is reduced. More specifically, when the sample cell 107 is replaced, signal deterioration can be suppressed by moving the sample cell 107 and the reflection member 108 with a stage 117 to positions in the optical axis (X-axis) direction at which the light amount of the probe light L2 detected at the detector 111 becomes maximum.

Further, the detector 111 is not limited to a general detector formed of only the pinhole 115 and the light receiving element 116, and may also be a detector adopting an astigmatic method, a knife edge method, and the like.

Second Embodiment

Next, a second embodiment will be described.

Figure 4:
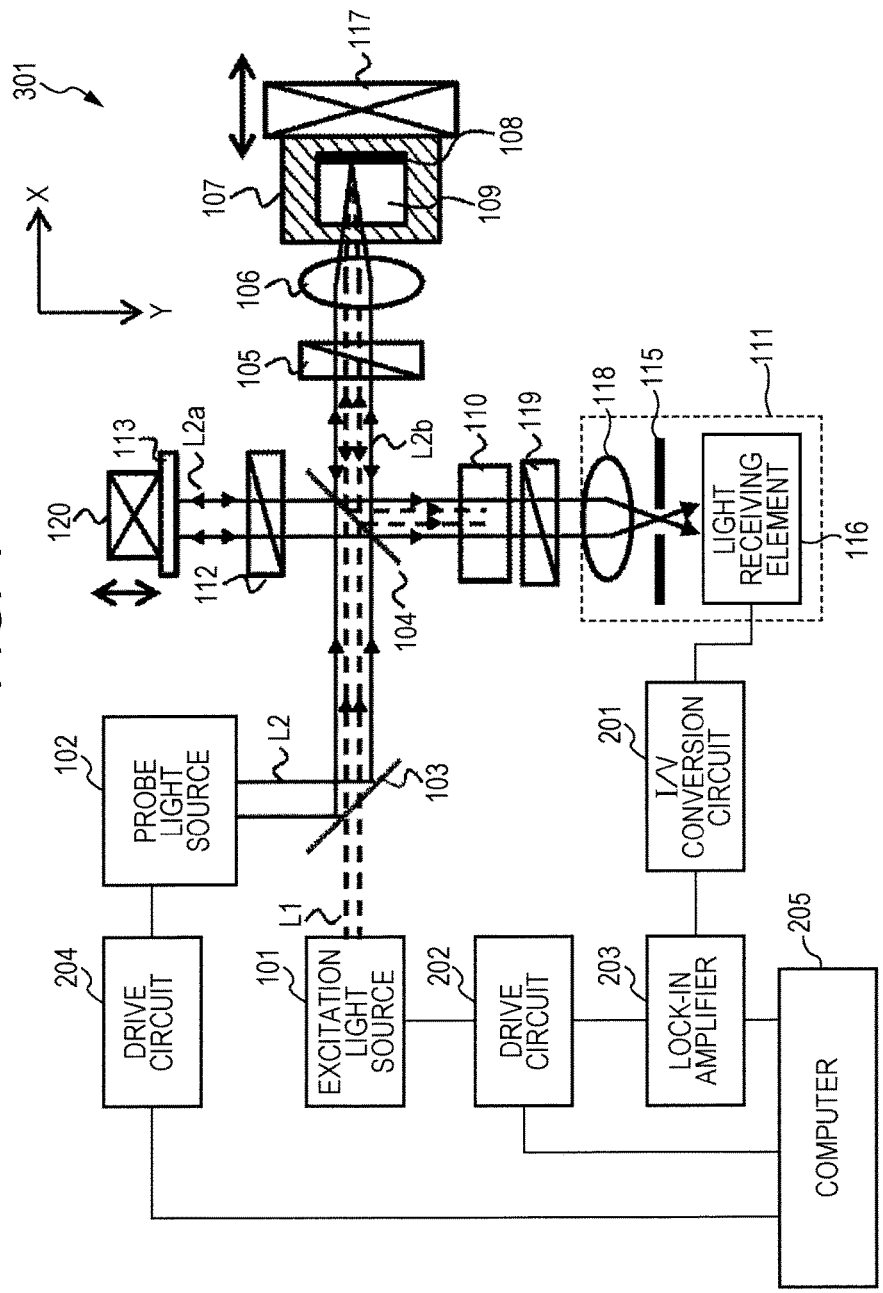
FIG. 4 is a configuration diagram illustrating a photothermal conversion spectroscopic analyzer 301 according to a second embodiment.

FIG. 4 is a configuration diagram illustrating a photothermal conversion spectroscopic analyzer 301 according to the second embodiment. The basic configuration is same as a first embodiment. However, a configuration different from the first embodiment is that a probe light L2 emitted from a probe light source 102 is divided into two at a second filter 104 on the way of being emitted to a sample 109, and the divided lights are multiplexed again on a same optical axis. In the following, the points different from the first embodiment in a sample analysis method using the photothermal conversion spectroscopic analyzer 301 according to the second embodiment will be described.

The probe light L2 emitted from the probe light source 102 is reflected at a first filter 103 and then divided into a probe light L2a and a probe light L2b at the second filter 104.

The probe light L2a passes through a second quarter wavelength plate 112 in a reciprocating manner while the probe light L2a reflected at the second filter 104 is reflected at a reflector 113 and returns to the second filter 104 again, thereby rotating a polarization plane thereof by 90 degrees. Therefore, the probe light L2a subsequently passes through the second filter 104.

The probe light L2b having passed through the second filter 104 is reflected at a reflection member 108 same as the first embodiment, and after that, the probe light L2b is reflected at the second filter 104 and directed to a detector 111. The probe light L2a reflected at the reflector 113 and the probe light L2b reflected at the reflection member 108 are multiplexed on the same optical axis at the second filter 104.

Meanwhile, according to the second embodiment, the probe light L2a reflected at the reflector 113 and the probe light L2b reflected at the reflection member 108 are multiplexed at the second filter 104 to interfere with each other. In order to make the probe light L2a and the probe light L2b favorably interfere with each other at the position of the second filter 104, preferably a wavefront of the probe light L2b is formed same as a wavefront of the probe light L2a in a state that no thermal lens is generated. More specifically, the wavefront of the probe light L2b can be formed same as a plane wave of the probe light L2a at the position of the second filter 104 by matching a focusing position of the probe light L2b to be focused at a first condenser lens 106 with the position of the reflection member 108 in an X-axis direction.

Figure 5:
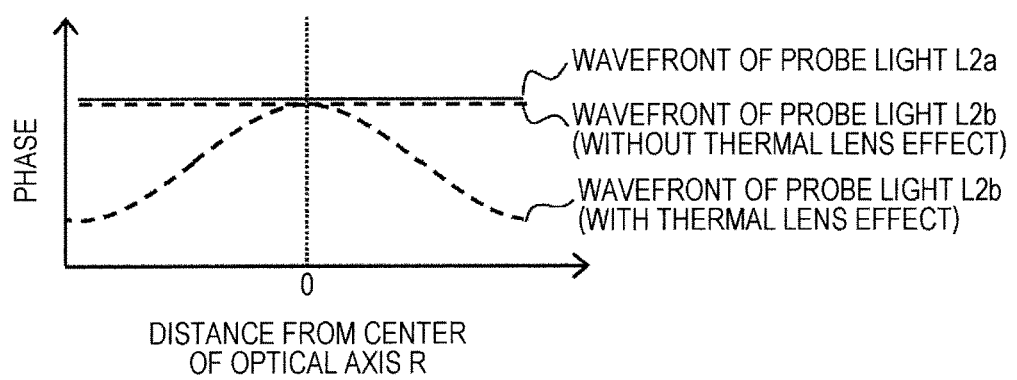
FIG. 5 is a schematic diagram illustrating wavefronts of a probe light L2a and a probe light L2b entering a filter.
Figure 6A:
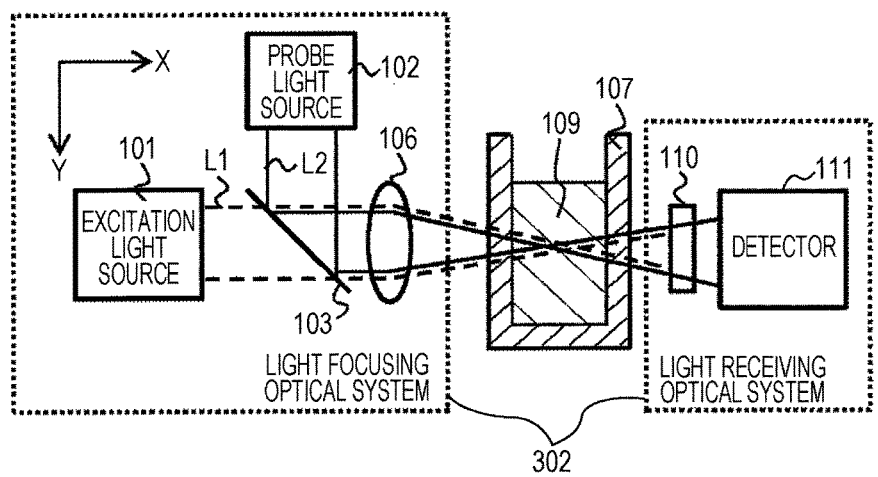
FIGS. 6A and 6B are schematic configuration diagrams illustrating a conventional photothermal conversion spectroscopic analyzer using a thermal lens effect.
Figure 6B:
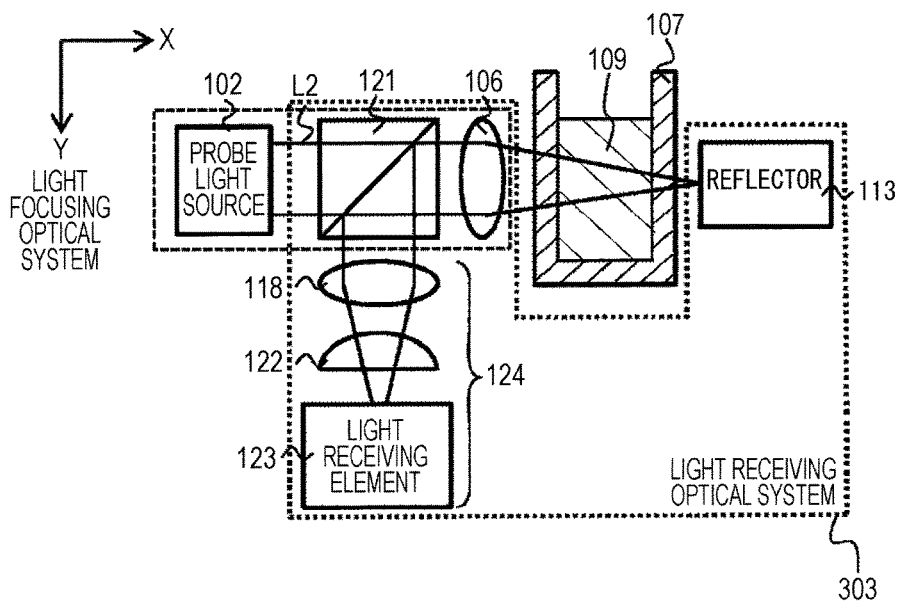

FIG. 5 illustrates Y-axis cross-sectional wavefronts of the probe light L2a having passed through a polarization filter 119 and the probe light L2b.

The probe light L2a having passed the polarization filter 119 and the probe light L2b have the same polarization plane and have coherency. In an initial state in which no thermal lens is generated inside the sample 109, adjustment is made such that the wavefronts of the probe light L2a having passed through the polarization filter 119 and the probe light L2b become same by moving the reflector 113 in the optical axis (Y-axis) direction with a stage 120. In the case where no thermal lens is generated inside the sample 109, both the probe light L2a and the probe light L2b are parallel lights. Therefore, the wavefronts of the probe light L2a having passed through the polarization filter and the probe light L2b are constant and have high coherency, and coherent light intensities are strong.

However, as illustrated in FIG. 2, when the thermal lens acting as a concave lens is generated inside the sample 109 located in the middle of an optical path, the probe light L2b having a focal point connected to the reflection member 108 inside the sample cell 107 has the focal position moved in a negative X-direction. As a result, the probe light L2b that has been reflected at the reflection member 108 and passed through the first condenser lens 106 (indicated by dotted lines in FIG. 2) is returned to a first quarter wavelength plate 105 as a divergent light, and the wavefront thereof has a phase varied by a distance from a center of the optical axis. Therefore, the coherent light intensities of the probe light L2a having passed through the polarization filter and the probe light L2b are varied by the distance from the center of the optical axis, and a light amount of an entire light flux is reduced. Then, the probe light L2a having passed through the polarization filter 119 and the probe light L2b are detected by the detector 111 in the same manner as the first embodiment.

According to the present embodiment, change of a receiving light amount due to change of a focusing angle/divergent angle of the probe light L2 is detected by the detector 111 same as the first embodiment, but in the present embodiment, the light amount change caused by the phase change is further superimposed. Therefore, there is a characteristic in which the light amount change detected by the detector 111 is increased when the thermal lens is generated inside the sample 109.

REFERENCE SIGNS LIST

101 Excitation Light Source
102 Probe Light Source
103 First Filter
104 Second Filter
105 First Quarter Wavelength Plate
106 First Condenser Lens
107 Sample Cell
108 Reflection Member
109 Sample
110 Third Filter
111 Detector
112 Second Quarter Wavelength Plate
113 Reflector
115 Pinhole
116 Light Receiving Element
117 Stage
118 Second Condenser Lens
119 Polarization Filter
120 Stage
121 Filter
122 Cylindrical Lens
123 Light Receiving Element
124 Detector
201 Current/Voltage Conversion Circuit
202 Drive Circuit For Excitation Light Source
203 Lock-In Amplifier
204 Drive Circuit For Probe Light Source
205 Computer
L1 Excitation Light
L2 Probe Light
300-303 Photothermal Conversion Spectroscopic Analyzer

What is claimed is:

1. A photothermal conversion spectroscopic analyzer, comprising:
    an excitation light source;
    a probe light source;
    a first filter configured to mutually multiplex a probe light emitted from the probe light source and an excitation light emitted from the excitation light source to a same optical axis that runs in a horizontal direction;
    a second filter configured to divide the probe light into a first probe light and a second probe light, wherein the first probe light runs approximately along the optical axis and the second probe light runs approximately along a vertical axis that is approximately orthogonal relative to the optical axis;
    a first condenser lens configured to focus the first probe light and the excitation light;
    a sample cell configured to store a sample;
    a reflection member disposed on an inner wall of the sample cell irradiated with the first probe light having passed through the sample and configured to reflect the first probe light;
    a detector configured to detect a probe light obtained by multiplexing the second probe light reflected at the reflector and the first probe light reflected at the reflection member; and
    a stage disposed on an outer wall of the sample cell on a same side as the disposed reflection member, the stage configured to move the sample cell and the reflection member in a left or right direction along the horizontal direction of the optical axis, and
    wherein the sample contacts the reflection member.

* * * * *